United States Patent [19]
Kinoshita

[11] 3,986,692
[45] Oct. 19, 1976

[54] APPARATUS FOR SUPPORTING ARTICLES

[75] Inventor: Kunio Kinoshita, Hachioji, Japan

[73] Assignee: Olympus Optical Co., Ltd., Tokyo, Japan

[22] Filed: Mar. 27, 1975

[21] Appl. No.: 562,674

[30] Foreign Application Priority Data
Apr. 4, 1974  Japan.............................. 49-38317
Apr. 4, 1974  Japan......................... 49-38623[U]

[52] U.S. Cl.................................. 248/160; 60/481
[51] Int. Cl.²......................................... F16M 13/00
[58] Field of Search .......... 248/274, 160, 276, 400, 248/169; 285/106, 166, 261; 403/15, 31; 52/108, 109, 110, 111; 60/481; 417/279

[56] References Cited
UNITED STATES PATENTS

| | | | |
|---|---|---|---|
| 1,827,432 | 10/1931 | Hundemer.......................... | 285/166 |
| 2,638,362 | 5/1953 | Sherman et al...................... | 285/105 |
| 2,693,378 | 11/1954 | Beyer................................... | 285/105 |
| 3,001,367 | 9/1961 | Bartholomew........................ | 60/481 |
| 3,168,274 | 2/1965 | Street................................... | 248/260 |
| 3,255,587 | 6/1966 | London................................ | 60/481 |
| 3,529,797 | 9/1970 | Street................................... | 248/160 |
| 3,584,822 | 6/1971 | Oram.................................... | 248/160 |
| 3,638,973 | 2/1972 | Poletti................................. | 248/276 |

Primary Examiner—Robert A. Hafer
Attorney, Agent, or Firm—Ostrolenk, Faber, Gerb & Soffen

[57] ABSTRACT

An apparatus for supporting articles comprises a deformable, rod-shaped support assembly including a plurality of links interconnected by articulated joints, a plurality of constrictor plates each disposed at the respective articulated joint of the links, the constrictor plates being operable to lock or unlock the articulated joints in response to a hydraulic pressure applied thereto, a base for supporting the support assembly, one end of the support assembly being anchored to the base by a connector, a communication passage extending through the links and their associated articulated joints from said one end to the free end of the support assembly, hydraulic supply means for admitting or displacing hydraulic fluid into or from the communication passage through a path in the base, an article mount fixedly connected with the free end of the support assembly for detachably mounting an article thereon. When the hydraulic pressure within the communication passage is reduced, the articulated joints associated with the respective links are released from the constrictor plates for free movement, thereby enabling the attitude of the support assembly to be changed by externally deflecting or bending it. Conversely, when the hydraulic pressure within the communication passage is increased, the constrictor plates lock the articulated joints between adjacent links, whereby the support assembly is maintained immobile.

7 Claims, 5 Drawing Figures

APPARATUS FOR SUPPORTING ARTICLES

BACKGROUND OF THE INVENTION

The invention relates to an apparatus for supporting articles.

When assembling, repairing, machining or operating a mechanical instrument having a complex and elongate structure such as an endoscope or other articles having a voluminous structure, it will be highly convenient if the instrument or article is mounted on a freely deflectable or deformable support assembly so as to permit the intended operation while changing the position or orientation of the article through a proper deflection or deformation of the support assembly. A conventional apparatus of this kind comprises a plurality of links connected together by means of joints, which are tightened by bolting. Hence, when changing the position of the support assembly, all of the bolts must be loosened by an amount sufficient to permit a desired deflection at the location of the respective joints and then tightened when a desired position is obtained, thereby requiring a tremendously labor consuming operation. The extent to which the overall support assembly can be deflected or deformed can be conveniently increased by increasing the number of joints used, but this results in a further increase in the amount of labor necessary for loosening or tightening the bolts. Thus, the number of joints has been necessarily limited in conventional apparatus.

SUMMARY OF THE INVENTION

It is an object of the invention to provide an apparatus for supporting articles in which a rod-shaped support assembly is formed by a plurality of links interconnected by articulated joints, which are controlled by a plurality of constrictor plates associated with the respective joints, the constrictor plates being operated by pressure control of a hydraulic fluid which is supplied to a communication passage extending through the links and the articulated joints across the opposite ends of the support assembly, thereby enabling the pressure control of the hydraulic fluid to cause a deflection or deformation and an immobilization of the support assembly to be quickly achieved in a very simple manner.

In accordance with the invention, pressure control of the hydraulic fluid achieves a uniform control of the constrictor plates located within the articulated joints of the respective links in a single operation, so that the bending and immobilization of the support assembly is accomplished in a rapid manner and is greatly simplified. Thus, an increase in the number of the articulated joints does not result in a more complex operation, thereby affording the possibility that the position or attitude of the support assembly can be rapidly changed into a variety of directions and to varying degrees especially as compared with conventional apparatus.

In accordance with a further aspect of the invention, the support assembly is anchored to a base by a connector within which a stop valve is located for blocking a communication path extending between the support assembly and the base in the event the assembly is dismounted from the base. Thus no leakage of the hydraulic fluid occurs in either the support assembly or the base, thereby enabling a simple removal or replacement or exchange of the support assembly.

DETAILED DESCRIPTION OF THE PREFERRED EMBODIMENT

Figure 1:
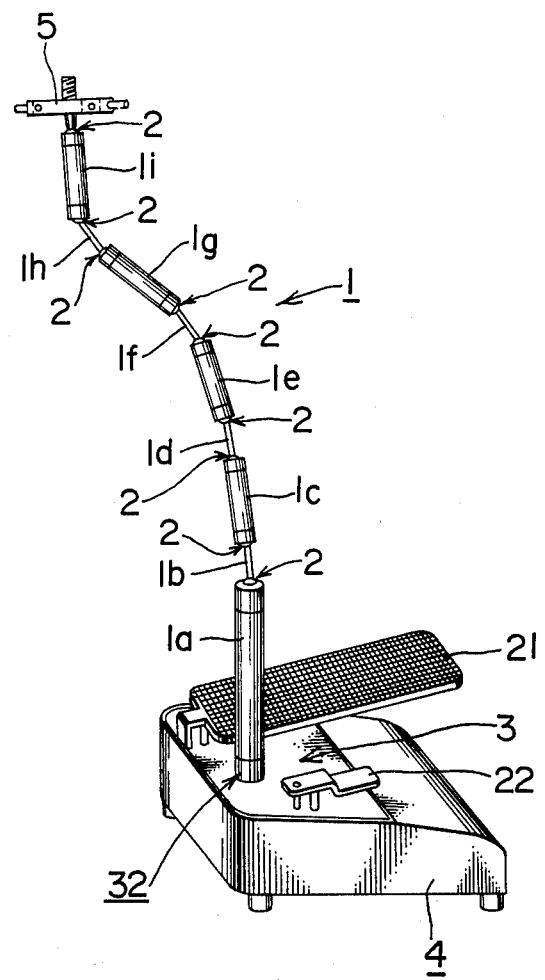
FIG. 1 is a perspective view of the apparatus for supporting articles constructed in accordance with one embodiment of the invention.

Referring to FIG. 1, a rod-shaped support assembly 1 comprises a plurality of links 1a, 1b, 1c ... 1h, 1i which are interconnected by articulated joints 2 to be described later. The lower end of the support assembly 1 is detachably mounted on a base 4 by anchoring the lower end of the link 1a to the base 4 by means of a connector 32 to be described later. A control panel 3 is mounted on the upper surface of the base 4 for remote control of the articulated joints 2.

An article mount 5 is mounted on the free end or the upper end, as viewed in FIG. 1, of the support assembly 1 by connecting its bottom portion with the upper end of the link 1i through the articulated joint 2. An endoscope, tool, or any other instrument (not shown) may be detachably mounted on the mount 5 by known suitable means.

Figure 2:
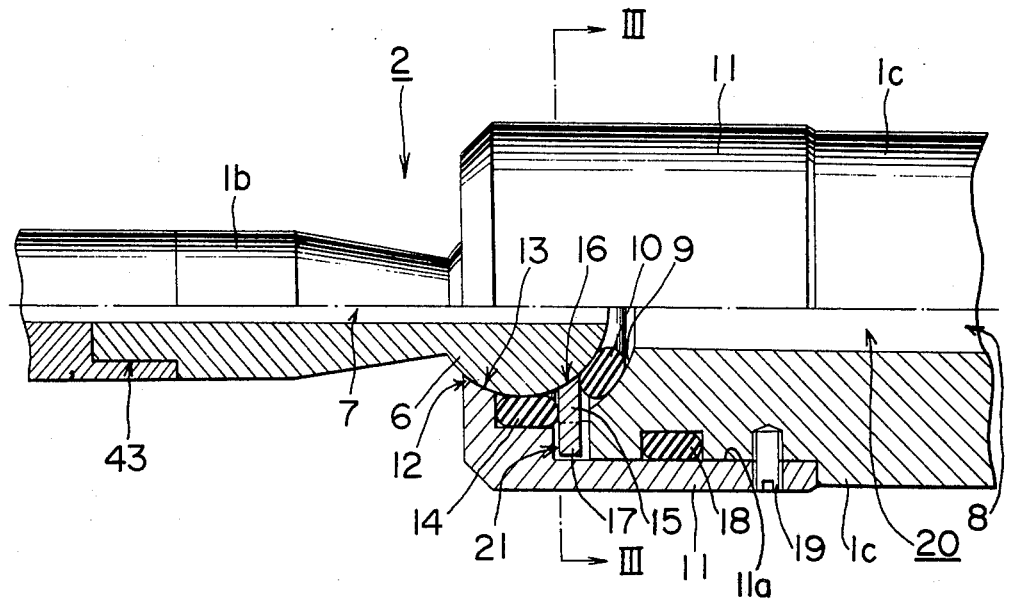
FIG. 2 is a side elevation, partly in section, of a pair of links and an articulated joint therebetween.
Figure 3:
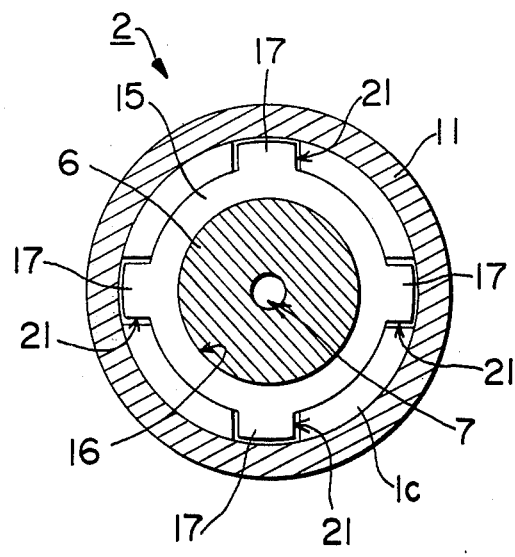
FIG. 3 is a cross section taken along the line III—III shown in FIG. 2.

Referring to FIGS. 2 and 3, there is shown one of the articulated joints 2 which is used between the links 1b and 1c. One of the links, 1b, is provided with a spherical shaped connecting member 6 at its ends and is internally formed with a communication path 7 extending lengthwise, said path also extending through the end of the connecting member 6. The other link 1c is also internally formed with a lengthwise extending communication path 8, which is sharply tapered outwardly at its opposite ends (only the left-hand end of the link 1c being shown), forming an enlarged area 9 for receiving the connecting member 6. The connecting member 6 is fitted into the enlarged area 9 with an O-ring 10 interposed therebetween, and the member 6 is rotatably retained in place by a connecting cap 11 which is threadably engaged in the region 11a with the left-hand end of the link 1c. Specifically, the cap 11 is cylindrical in configuration so as to be fitted over the end of the link 1c which is adjacent to the link 1b, and is formed with an opening 12 at its one end which receives the link 1b. The link 1b is formed in two parts in its right-hand end portion, which parts can be separated at 43 to insert the connecting member 6 into the cap 11 and thereafter joined together. The opening 12 defines a part-spherical seat 13 for surface contact with the spherical member 6, thus retaining it in place.

The inner periphery of the connecting cap 11 is stepped, and an O-ring seal 14 is interposed between a maximum diameter portion of the connecting member 6 and a portion of the cap 11 which has a reduced inner diameter, thereby hermetically sealing the clearance between the member 6 and the cap 11. An annular constrictor plate 16 is disposed between the O-rings 14 and 10, and has an active edge 16 which surrounds the foremost portion of the connecting member 6 for surface contact therewith. As shown in FIG. 3, the constrictor plate 15 is provided with a plurality of detent fingers 17 which extend from the outer periphery thereof, the detent fingers being loosely fitted into detent grooves 21 formed in an end region of the link 1c which projects beyond the enlarged area 9. An annular groove is formed in the outer periphery of the link 1c so as to receive an O-ring seal 18, and the cap 11 is secured to the link 1c by means of a set screw 19. In this manner, when the links 1b and 1c are connected, their communication paths 7, 8 communicate with each other, thereby forming a portion of a communication passage 20 extending through the support assembly 1.

The respective links 1a, 1b, 1c . . . 1i are successively connected together through the articulated joints in the manner mentioned above (see FIG. 1). Specifically, the links 1a, 1e, 1g and 1i are similar in construction to the link 1c while the links 1d, 1f, 1h and the lower portion of the article mount 5 are similar in construction to the link 1b. At its other end, the link 1b is provided with a similar connecting member which connects with the link 1a, and the other end of the link 1c is provided with a similar connecting cap which connects with the adjacent link 1d, which in turn connects with the link 1e and so on. The link 1a has its one end detachably secured to the base 4 through a connector to be described later, and its communication path is connected with hydraulic fluid supply means 42 (see FIG. 4). The mount 5 is connected with the forward end of the link 1i through a similar articulated joint 2, and a communication path therein is blocked intermediate its length. Thus, the communication passage 20 extending through the links 1a to 1i is connected at its one end with the hydraulic fluid supply means 42 while its other end is blocked.

Figure 4:
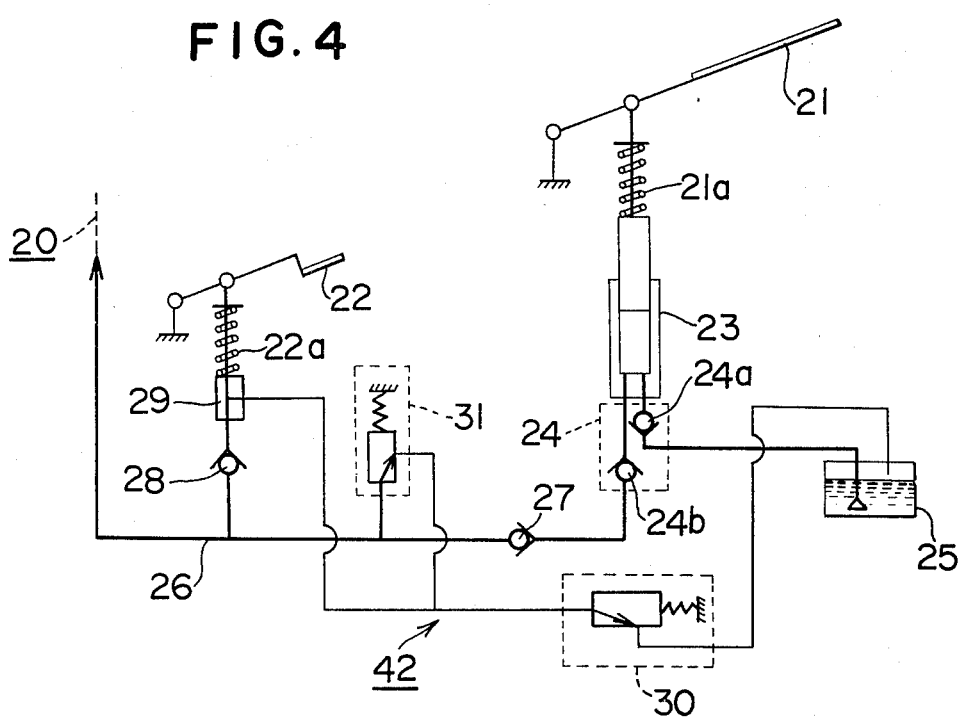
FIG. 4 is a schematic diagram illustrating the paths of the hydraulic fluid in the hydraulic fluid supply means.

The hydraulic fluid supply means 42 is disposed within the base 4 and has a fluid circuit as shown in FIG. 4. A foot pedal 21 is provided on the control panel 3 (see FIG. 1) and can be depressed to increase the pressure of the hydraulic fluid supplied to the communication passage 20. Another foot pedal 22 is also disposed on the control panel 3 and can be depressed to displace the hydraulic fluid from the communication passage 20, thus reducing the pressure thereof. The pedal 21, when depressed, drives a plunger pump 23 which in turn operates on a valve unit 24 including a suction valve 24a and a discharge valve 24b so as to admit and pressurize fluid from a fluid tank 25 and deliver it to the communication passage 20 through a conduit 26. A check valve 27 is connected in the conduit 26.

The other pedal 22 operates on a vent valve 29 which communicates with the conduit 26 through a check valve 28, the vent valve 29 being connected with the fluid tank 25 through a relief valve 30. Thus, when the pedal 22 is depressed to open the vent valve 29, the hydraulic fluid within the communication passage 20 is drained to the tank 25 through the relief valve 30. The purpose of the relief valve 30 is to retard the rate of return flow of the fluid in order to prevent rapid relaxation and collapse of the support assembly 1. Another relief valve 31 is connected with the tank 25 in series with the relief valve 30 so as to secure the communication passage 20 and the supply means 42. It will be noted that both pedals 21, 22 are respectively normally urged in an upward direction by means of coiled springs 21a, 22a.

Figure 5:
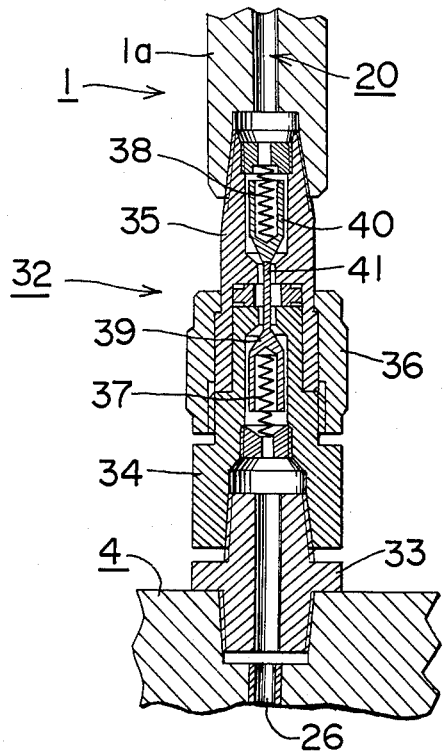
FIG. 5 is a cross section of the connector located between the support assembly and the base.

The conduit 26 for the hydraulic fluid supply means 42 is connected with the communication passage 20 within the support assembly 1 through a connector 32 shown in FIG. 5. Specifically, the base 4 is threadably engaged by a fitting 33 onto which is screwed a coupler 34. Another coupler 35 is screwed into the lower end of the link 1a in the support assembly 1, and the couplers 34, 35 are detachably connected together by a coupling ring 36. A pair of springs 37, 38 are internally housed within the respective couplers 34, 35 for urging valve elements 39, 40 received within the respective couplers so that the path through the couplers 34, 35 is blocked when the couplers are separated from each other. However, when the couplers 34, 35 are connected together, a pin 41 projecting upwardly from one of the valves, 39, extends between the valve elements 39, 40 to prevent a blocking action of these valve elements. Thus when the couplers 34, 35 are connected together, the communication passage 20 within the support assembly 1 is automatically connected with the conduit 26 located in the base 4, while when the couplers 34, 35 are separated from each other, the communication between the conduit 26 and the communication passage 20 is automatically interrupted, thereby allowing a detachable mounting of the support assembly 1 on the base 4 while preventing an effluence of the hydraulic fluid therefrom. As a result, a number of different support assemblies 1 may be provided depending on the variety of articles to be supported, and can be selectively mounted on the base 4, thereby improving the operational efficiency. It is to be noted that either one of the valve elements 39, 40 may be omitted. In this instance, in consideration of the provision of the check valves 27, 28 in the fluid circuit, it is preferred that the valve element which is to be left is provided within the coupler 35 in the support assembly 1. In addition to oil, the fluid for supplying the pressure to the communication passage may be air or water, and in such instance, the valve elements 39, 40 need not be provided.

In operation, the pedal 21 is preferably depressed by the operator's foot to drive plunger pump 23, thereby pumping the oil from the fluid tank 25 into the communication passage 20. Thereupon, the connecting members 6 of the respective articulated joints 2 are immobilized as a result of the clamping engagement of the connecting members 6 with the constrictor plates 15. Specifically, as the pressure is increased, the fluid urges the O-ring 10 of each link downward to displace its associated constrictor plate 15 toward the maximum diameter portion of the connecting member 6, so that the active edges 16 thereof are strongly pressed against the peripheral surface of the connecting member 6. The force of friction acting between the connecting member 6 and the active edges 16 is effective to immobilize the member 6. On the other hand, when the pedal 22 is depressed to open the vent valve 29 so as to displace the hydraulic fluid within the communication passage 20 to the fluid tank 25, the pressure therein is reduced, whereby the constrictor plates 15 are no longer urged against the member 5 so strongly as before, thereby reducing the force of friction between the member 6 and the active edge 16. Consequently, the respective links can be freely articulated in any desired direction. It is desirable, however, that the freedom of movement imparted to the joints upon reduction of the pressure be limited so as to prevent a collapse of the support assembly 1. After adjusting the links to a desired position, the pedal 21 is again depressed to pressurize the communication passage 20, thereby immobilizing the respective joints 2 in a single operation.

While in the above desired embodiment, the articulated joints have been described as comprising a pair of elements which engage along a spherical surface, the type of such contact may be changed in any desired manner. For example, a pair of links may be connected together by a pin with the surfaces of frictional engagement being urged toward each other under hydraulic pressure, thus forming a pair of elements engaging along a cylindrical surface. While a pair of foot pedals 21, 22 are shown on the base 4, a single foot pedal may be provided so as to change the pressure depending on the direction or the angle of rotation thereof. Obviously, the hydraulic fluid supply means 42 may be separate from the base 4 either partly (such as only the fluid tank 25) or entirely and connected with the base 4 by a suitable conduit. Also the hydraulic fluid supply means 42 can be controlled electrically by providing a combination of an electric motor and a compressor, for example.

What is claimed is:

1. An apparatus for supporting articles comprising a generally rod-shaped, deformable support assembly including a plurality of links connected together by articulated joints, a plurality of rigid constrictor plates each associated with the respective articulated joints, a base for supporting the article support assembly, a connector for anchoring the lower end of the support assembly to the base, a communication passage extending through the respective links and their associated articulated joints across the opposite ends of the support assembly, hydraulic fluid supply means for admitting or displacing a hydraulic fluid into or from the communication passage through a path in the base, and an article mount secured to the free end of the article support assembly for detachably mounting an article thereon, each of the articulated joints comprising a spherical connecting member formed at one end of a link which is to be connected with another link through the joint, an enlarged area formed in the adjacent end of said other link, a cap fitted over said end of said other link for retaining said one link to be freely pivotable relative to said other link when said connecting member is received in said enlarged area while preventing said links from being separated, each of the plurality of constrictor plates being disposed in said enlarged area around an associated connecting member, and an annular resistant sealing ring disposed against the constrictor plate, said constrictor plate being responsive to the pressure level of hydraulic fluid applied thereto through the sealing ring for selectively locking or unlocking the connecting member, a second sealing ring disposed in each connecting member and normally biasing its associated constrictor plate towards an unlocking position with said constrictor plate, said constrictor plates selectively locking or unlocking the respective articulated joints in response to a change in the pressure of the hydraulic fluid supplied to the communication passage.

2. An apparatus for supporting articles according to claim 1 in which the said connector comprising a pair of couplers each associated with the base and the support assembly, respectively, and adapted to be threadably engaged with each other, a pair of valve elements disposed within the restrictive couplers, spring means for urging said pair of valve elements toward positions in which a flow path within the respective couplers are blocked and an abutment pin interposed between said pair of valve elements, said spring means urging the valve elements towards said positions so as to block the flow path within the couplers when both couplers are separated from each other, said abutment pin being effective to limit movement of the valve elements toward each other when said pair of couplers are connected together, whereby the flow paths within the respective couplers communicate with each other.

3. An apparatus according to claim 1 in which the hydraulic fluid supply means comprises a fluid tank containing a supply of hydraulic fluid, control means for increasing or reducing the pressure of the hydraulic fluid within the communication passage, first check valve means for permitting flow of hydraulic fluid in a first direction from said supply and for preventing a reverse flow of the hydraulic fluid to thereby maintain the pressure level applied to the links from the supply by the control means, and a relief valve for preventing a rapid reduction in the pressure of the hydraulic fluid.

4. An apparatus for supporting articles according to claim 3 in which said control means comprises a plunger pump operated by a pressure generating foot pedal assembly mounted on said base, and a second relief valve operated by a pressure reducing foot pedal assembly mounted on said base.

5. The apparatus of claim 3 wherein said control means further comprises second valve means and second manually operable means for operating said valve means to release said hydraulic pressure, said second valve means comprising means for slowly releasing the hydraulic pressure regardless of the manner of operation of said second manually operable means.

6. An apparatus for supporting articles comprising:
   a base;
   a generally rod-shaped, deformable support assembly having a plurality of links connected together by articulated joints;
   a plurality of rigid constrictor plates each associated with the respective articulated joints;
   a connector member for anchoring the lower end of the support assembly to said base;
   each of the respective links having a hollow passageway communicating with all of the adjacent links and their associated articulated joints to cooperatively form a continuous passage extending between the opposite ends of the support assembly;
   hydraulic fluid supply means for admitting or displacing a hydraulic fluid into or from the continuous passage and including a pathway extending between the hydraulic fluid supply means and the support assembly through said base member;
   an article mount secured to the free end of the article support assembly for detachably mounting an article thereon;
   each of said joints comprising a spherical connecting member formed at one end of each link which is to be connected with an adjacent link through said joint;
   an enlarged area formed in the adjacent end of said other link;
   a cap fitted over said end of said other link and embracing said spherical connecting member to retain said one link to said other link to be freely swingable relative to said other link when said connecting member is received in said enlarged area, while preventing said links from being separated from one another;

a rigid constrictor plate being provided within each joint and disposed in said enlarged area so as to surround an associated spherical connecting member;

first and second annular resilient sealing rings disposed on opposite sides of each constrictor plate;

one of said rings being adapted to normally urge its associated constrictor plate away from said spherical member while the remaining annular ring is adapted to be urged against said constrictor plate responsive to an increase in the pressure level of hydraulic fluid applied thereto for urging the constrictor plate into intimate contact with the spherical connecting member and thereby lock the joint;

first valve means connected between said fluid supply means and said article support assembly being adapted to admit the flow of hydraulic fluid from said supply means into said article support means while preventing the reverse flow of hydraulic fluid thereby maintaining the article support means in locked fashion when the hydraulic fluid within the article support means reaches a predetermined pressure level;

second pressure release control means comprising second normally closed valve means coupled between said fluid supply means and said article support means and including manually operable means for opening said valve means to relieve the fluid pressure in said article support means whereupon each of said first sealing rings disengages its associated constrictor plate from the spherical connecting member to permit the article support means to be reoriented in any desired configuration.

7. The apparatus of claim 6 wherein said second control means further comprises slow release valve means coupled between said normally closed valve means and said fluid supply means for causing slow release of the fluid pressure in the article support means so as to prevent immediate collapse thereof.

* * * * *